United States Patent
Kawamura

(10) Patent No.: US 6,468,076 B2
(45) Date of Patent: Oct. 22, 2002

(54) ORAL CAVITY WASHER WITH VIDEO SCOPE

(75) Inventor: Taturou Kawamura, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/774,339

(22) Filed: Jan. 31, 2001

(65) Prior Publication Data

US 2001/0012605 A1 Aug. 9, 2001

(30) Foreign Application Priority Data

Jan. 31, 2000 (JP) .................................. 2000-022852

(51) Int. Cl.[7] ................................................ A61C 1/00
(52) U.S. Cl. ........................................... 433/29; 433/80
(58) Field of Search .............................. 433/29, 30, 31, 433/80

(56) References Cited

U.S. PATENT DOCUMENTS

| 2,228,169 A | | 1/1941 | Keogh, Jr. et al. | |
|---|---|---|---|---|
| 3,027,644 A | * | 4/1962 | Piscitelli | 433/30 |
| 4,080,476 A | * | 3/1978 | Laskey | 433/30 |
| 4,655,198 A | | 4/1987 | Hommann | 433/80 |
| 5,178,536 A | * | 1/1993 | Werly et al. | 433/29 |
| 5,328,365 A | * | 7/1994 | Jacoby | 433/29 |
| 5,484,283 A | * | 1/1996 | Franetzki | 433/29 |
| 5,634,790 A | * | 6/1997 | Pathmanabhan et al. | 433/29 |
| 5,743,731 A | * | 4/1998 | Lares | 433/29 |
| 6,102,695 A | * | 8/2000 | Rosenstatter | 433/29 |

FOREIGN PATENT DOCUMENTS

| DE | 197 45 551 | 6/1998 |
|---|---|---|
| EP | 0 280 823 | 9/1988 |

* cited by examiner

*Primary Examiner*—Cary O'Connor
(74) *Attorney, Agent, or Firm*—RatnerPrestia

(57) ABSTRACT

An oral cavity washer with a video scope, has a video scope having image-forming means of forming an image from light from an object, an image pick-up device for converting the light from which the image is formed by the image-forming means into an electric signal, and a first grip portion for being held by an operator;

a display for displaying an image picked up by the video scope; and an oral cavity washer having a nozzle for jetting a fluid and a second grip portion for being held by the operator, for washing an oral cavity by jetting the fluid to teeth or gums, wherein the first grip portion and the second grip portion are capable of being made integral with each other.

15 Claims, 5 Drawing Sheets

ORAL CAVITY WASHER WITH VIDEO SCOPE

BACKGROUND OF THE INVENTION

1. Field of the Invention

The present invention relates to a video scope incorporating an image pick-up device such as a CCD for picking up an image of an interior of an oral cavity, and an oral cavity washer for washing the interior of the oral cavity by jetting fluid such as water onto teeth or gums.

2. Related Art of the Invention

In recent years, a video scope using a CCD capable of picking up an image of a limited part while illuminating has been used for medical examination for a diseased part within the oral cavity in density, oral surgery and the like, and further for an operator to observe conditions of his own teeth or gums. In addition, in homes, there have become popular oral cavity washers for jetting water onto the teeth or gums with the aim of washing the interior of the oral cavity.

For a video scope for performing such local image pick-up and a nozzle portion for jetting liquid of the oral cavity washer, there is required one easy to handle, capable of being operated by holding by one hand.

Conventionally, the video scope and the oral cavity washer have been separately used. More specifically, teeth or gums attached with leftovers and the like are observed by the video scope, and after those are removed by jetting water to those portions, it is necessary to confirm the result with the video scope. In this case, it is difficult to actually confirm on an image that a place which an operator observed with the video scope, and a place, to which water was jetted, coincide with each other.

Also, since oral cavity washing is usually performed within a limited space such as a lavatory, it is often difficult in ordinary households to newly secure space to install a display for displaying a video scope image.

Further, in order to observe or wash all the teeth or gums thoroughly, complicated operations, such as shifting the video scope or the nozzle from one hand to the other or rotation, is necessary, and therefore, it is desirable to make it cordless.

SUMMARY OF THE INVENTION

The present invention has been achieved in the light of the above described points, and an object of the present invention is to provide an oral cavity washer with a video scope capable of washing the interior of the oral cavity while actually confirming on an image that a place which the operator observes with the video scope and a place, to which fluid is jetted, coincide with each other.

One aspect of the present invention is an oral cavity washer with a video scope, comprising:
  a video scope having image-forming means of forming an image from light from an object, an image pick-up device for converting the light from which the image is formed by said image-forming means into an electric signal, and a first grip portion for being held by an operator;
  a display for displaying an image picked up by said video scope; and
  an oral cavity washer having a nozzle for jetting a fluid and a second grip portion for being held by the operator, for washing an oral cavity by jetting said fluid to teeth or gums,
wherein said first grip portion and said second grip portion are capable of being made integral with each other.

A place where a liquid jetted for washing collides with an object, that is, teeth or gums, is located within the image pick-up range of the video scope, so that a washing operation can be performed while confirming a place to be washed on an image. In this manner, a place where this liquid is jetted is confirmed on the image while jetting liquid, whereby not only washing, but also a massage effect the gums and the like by pressure of water, can also be expected. Therefore the practical utility is improved.

Another aspect of the invention of the present invention is the oral cavity washer with a video scope wherein said display displays an aiming marker for indicating a reaching target point of said fluid jetted from said nozzle on an image picked up by said video scope.

Still another aspect of the present invention is the oral cavity washer with a video scope, further comprising a toothbrush portion having a brush portion and a third grip portion for being held by the operator, wherein said third grip portion and said first grip portion are capable of being made integral with each other.

Yet another aspect of the present invention is the oral cavity washer with a video scope, further comprising illuminating means of illuminating said object.

Still yet another aspect of the present invention is the oral cavity washer with a video scope, wherein said video scope has an optical window for transmitting light from said object, has further removal means of removing any deposit on said optical window, and said image-forming means forms an image from light from said object which transmits said optical window.

A further aspect of the present invention is the oral cavity washer with a video scope according to, wherein said removal means is jetting means of jetting the fluid.

A still further aspect of the present invention is the oral cavity washer with a video scope, wherein the fluid is alternately jetted onto said object and said optical window.

A yet further aspect of the present invention is the oral cavity washer with a video scope, wherein said nozzle serves as said jetting means.

A still yet further aspect of the present invention is the oral cavity washer with a video scope, wherein said nozzle causes said fluid to pulsate for jetting, and said fluid is alternately jetted to said object and said optical window in synchronism with the pulsation.

An additional aspect of the present invention is the oral cavity washer with a video scope, wherein a jetting velocity of the fluid to said optical window is controlled so as to be lower than a jetting velocity of the fluid to said object.

A still additional of the present invention is the oral cavity washer with a video scope, wherein said removal means is vibration means of vibrating said optical window.

A yet additional aspect of the present invention is the oral cavity washer with a video scope according to further comprising control means provided in said first grip portion, said second grip portion or said third grip portion, for controlling an operation of said removal means.

A still yet additional aspect of the present invention is the oral cavity washer with a video scope according to, wherein said optical window is subjected to a water-repellent treatment, which secures transmission of visible light.

A supplementary aspect of the present invention is the oral cavity washer with a video scope, wherein said water-repellent treatment uses dimethyl silicone-based organic polymer water repellant or silane coupling agent having straight alkyl chain.

A still supplementary aspect of the present invention is the oral cavity washer with a video scope according to wherein said optical window is subjected to a hydrophilic treatment, which secures transmission of visible light.

A yet supplementary aspect of the present invention is the oral cavity washer with a video scope according to, wherein said display is provided on a charger for charging an apparatus installed in said first grip portion or said second grip portion, or on an installation apparatus on which said first grip portion is installed when the washer is not used.

| Description of Symbols | |
|---|---|
| 1 | NOZZLE |
| 2 | PIPE |
| 3 | TUBE |
| 4 | ELECTRIC WIRE |
| 5 | GRIP PORTION |
| 6 | CONTROL SWITCH |
| 7 | VIDEO SCOPE BASE |
| 8 | CCD UNIT |
| 9 | OBJECTIVE LENS |
| 10 | PRISM MIRROR |
| 11 | WHITE LED |
| 12 | OPTICAL WINDOW |
| 13 | HEAD PORTION OF VIDEO SCOPE |
| 14 | HINGE |

PREFERRED EMBODIMENTS OF THE INVENTION

Hereinafter with reference to the drawings, embodiments of the present invention will be described.
(First Embodiment)

Hereinafter, with reference to FIGS. 1 to 3, the description will be made of an embodiment of the present invention.

In the present embodiment, the nozzle for jetting liquid to an object can be replaced with a toothbrush. These are replaced as required, whereby it becomes possible not only to perform washing for jetting liquid, but also to clean teeth by a toothbrush. By having this replacement function, the video scope can be utilized not only on jetting liquid, but also on cleaning teeth, which is effective.

Figure 1:
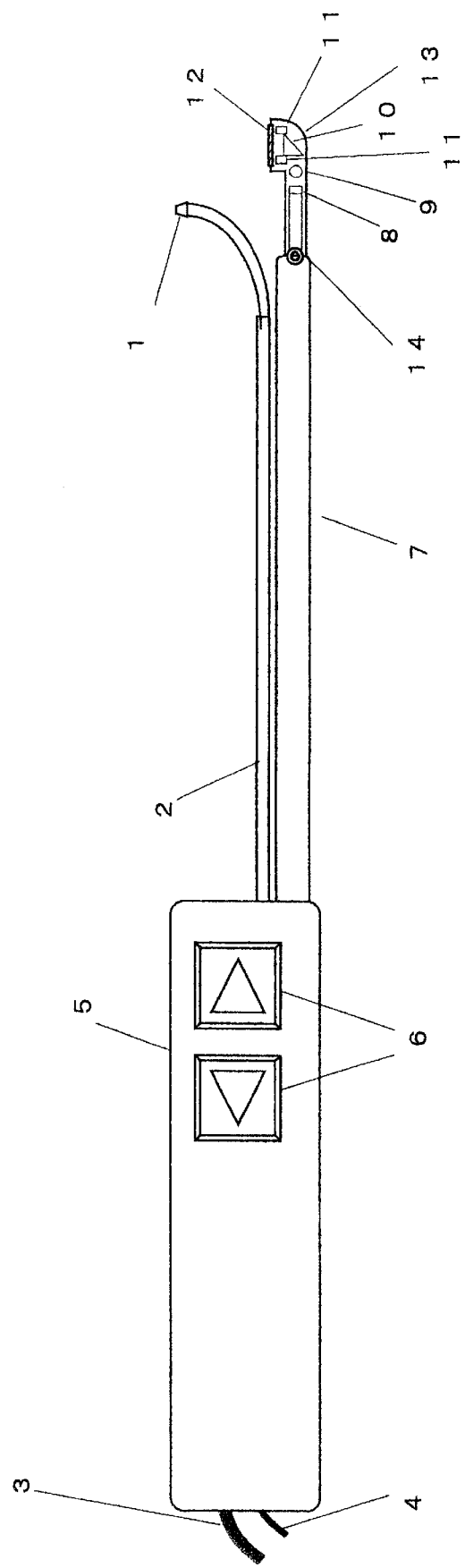
FIG. 1 is a side view showing a portion of an oral cavity washer with a video scope according to a first embodiment of the present invention.

FIG. 1 is a side view showing a portion of an oral cavity washer with a video scope according to the present embodiment. In FIG. 1, reference numeral 1 denotes a nozzle for jetting liquid, and reference numeral 2 denotes a pipe for supplying liquid to be jetted to the nozzle 1 and fixing the nozzle 1 to a grip portion 5. Reference numeral 3 denotes a tube for supplying liquid to the nozzle 1 from the main body 16 shown in FIG. 3 through the grip portion 5 and the pipe 2. Reference numeral 4 denotes electric wire for supplying power supply to the grip portion 5 and the video scope and transmitting a signal from the video scope to the main body 16.

In the grip portion 5, there are incorporated: a power battery; a toothbrush driving motor; a signal processing circuit for a video scope; an image transmission circuit; various control circuits and the like. Also, this grip portion 5 is provided with a control switch 6 for controlling an operation of the video scope, and jetting of the liquid, and driving of an electric toothbrush. Further, this grip portion 5 is mounted with a video scope base 7 for supporting a head portion 13 of the video scope.

Reference numeral 8 denotes a CCD unit in which a CCD, which is a solid state image pick-up device, is disposed at the tip end, and substrates for a driving circuit and a signal processing circuit are disposed at each terminal thereof. Reference numeral 9 denotes an objective lens, which forms an image on the light receiving surface of the CCD of the CCD unit 8. Reference numeral 10 denotes a prism mirror, to reflect pick-up light. An iris diaphragm is provided between the CCD unit 8 and the prism mirror 10 to adjust the angle of visibility, focal depth and the like, but is omitted in this drawing. The image-forming means is configured by the prism mirror 10, the iris diaphragm and the objective lens 9.

Reference numeral 11 denotes a white LED for illuminating the object. Reference numeral 12 denotes an optical window consisting of glass or the like which performs a waterproof function by hermetically sealing from the outside, and transmits visible light such that light from the object is capable of being incident to the prism mirror 10. A image pick-up system is configured by these CCD unit 8 and image-forming means. A head portion 13 of the video scope is configured by this image pick-up system and the illumination means (white LED 11). This head portion 13 is mounted to a video scope base 7 through a hinge 14, and the head portion 13 is tilted to an adequate angle about the hinge 14.

The video scope base 7 is fixed to the grip portion 5, and within the video scope base 7, electric wiring for supplying various signals and electric power is provided, but is omitted in this figure.

Figure 3:
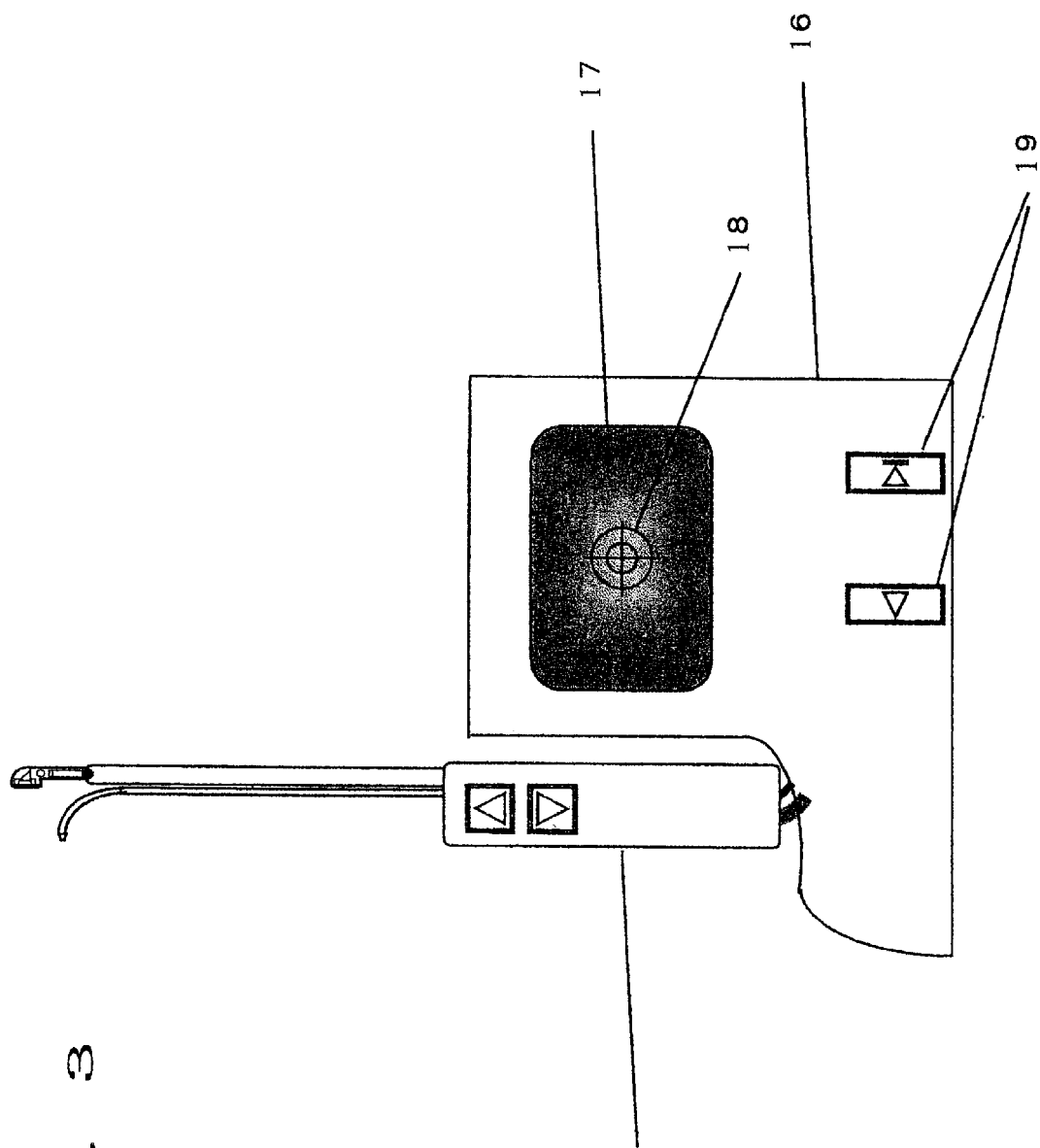
FIG. 3 is an overall view showing an oral cavity washer with a video scope according to each embodiment of the present invention.

The main body 16 of FIG. 3 is provided with a tank for accumulating liquid to be jetted, and a pump for sending the liquid within this tank to the nozzle 1 through the tube 3, which are omitted in this figure. An image picked up by the video scope is displayed on a display 17 provided on the main body 16. The main body 16 has also a charging function. This is also utilized as an installation apparatus when not used. Further, there are installed an image receiving circuit for receiving an image which has been picked up by the video scope and has been transmitted and a display circuit. These provide ease of operation and space saving, enabling spread in homes and the like to be promoted.

Each component of an oral cavity washer with a video scope according to the present embodiment is disposed as shown in FIG. 1, whereby it is possible to wash by jetting liquid while confirming an object tooth or gum on an image by using the video scope. Jetting of this liquid is controlled by a switch 6.

The portion ahead of the pipe 2 and the video scope base 7 enters the oral cavity to observe the tooth or gum on a display 17, and to wash by jetting liquid. In this washing, when the nozzle 1 and the object are located at a suitable distance, the angle of the head portion 13 and/or the position of an aiming marker 18 on the display 17 are adjusted in such a manner that a reaching target point of the liquid from the nozzle 1, that is, the object comes to the position of the aiming marker indicated by reference numeral 18 on the image of the display 17.

With this adjustment, an angle of visibility, a focal length and focal depth of the image-forming system, and an illumination angle and intensity of illumination means are adjusted in such a manner that the object can be clearly picked up to a suitable size. By displaying the aiming marker 18 on the image of the display 17 in this manner, the washing can be more effectively performed. On the main body 16, there is provided a switch 19 for adjusting the position of the aiming marker 18 and the jetting intensity. In this respect, when such an object as, for example, a specific tooth is clearly displayed on the display 17 and the object comes to the position of the aiming marker 18, it is structured such that the liquid from the nozzle 1 reaches the object.

Figure 2:
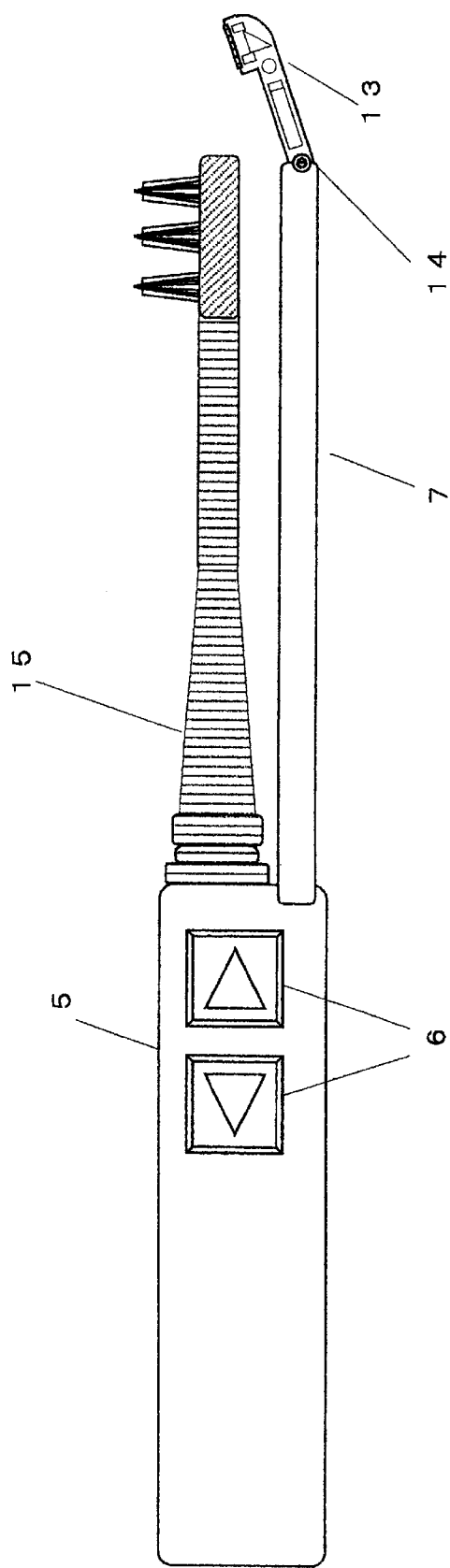
FIG. 2 is a view showing that an oral cavity washer in the oral cavity washer with a video scope of FIG. 1 has been replaced with a toothbrush.

When the nozzle 1 and the pipe 2 are removed from the grip portion 5 and the toothbrush 15 is installed to the toothbrush base of the grip portion 5 as shown in FIG. 2, it is also possible to clean the teeth by using the toothbrush. In this case, it is also possible to use by removing the tube 3. At this time, when the angle of the head portion 13 is adjusted such that the tip end portion of the brush comes within the image-forming range, it can be more easily used. Further, if the video scope is driven by the power supply within the grip portion 5 and the image is transmitted to the main body 16 through electromagnetic wave or the like, it will be able to be used by removing the electric wire 4. By making it cordless in this manner, the usability will be further improved.

As described above, it is possible to wash while actually confirming on the image that a place which has been observed with the video scope coincides with a place, to which the liquid is jetted, and the practical effect is very significant. Further, it is also possible to clean the teeth as required, which is effective.

In this respect, in the present embodiment, there has been shown an example in which the nozzle 1 and the pipe 2 have been removed on mounting the toothbrush 15, but it is not always necessary to do so. However, if the toothbrush 15, the nozzle 1 and the pipe 2 are arranged so as to be able to be mounted to the video scope at the same time, the grip portion 5 and the like will become larger in size.

(Second Embodiment)

Figure 4:
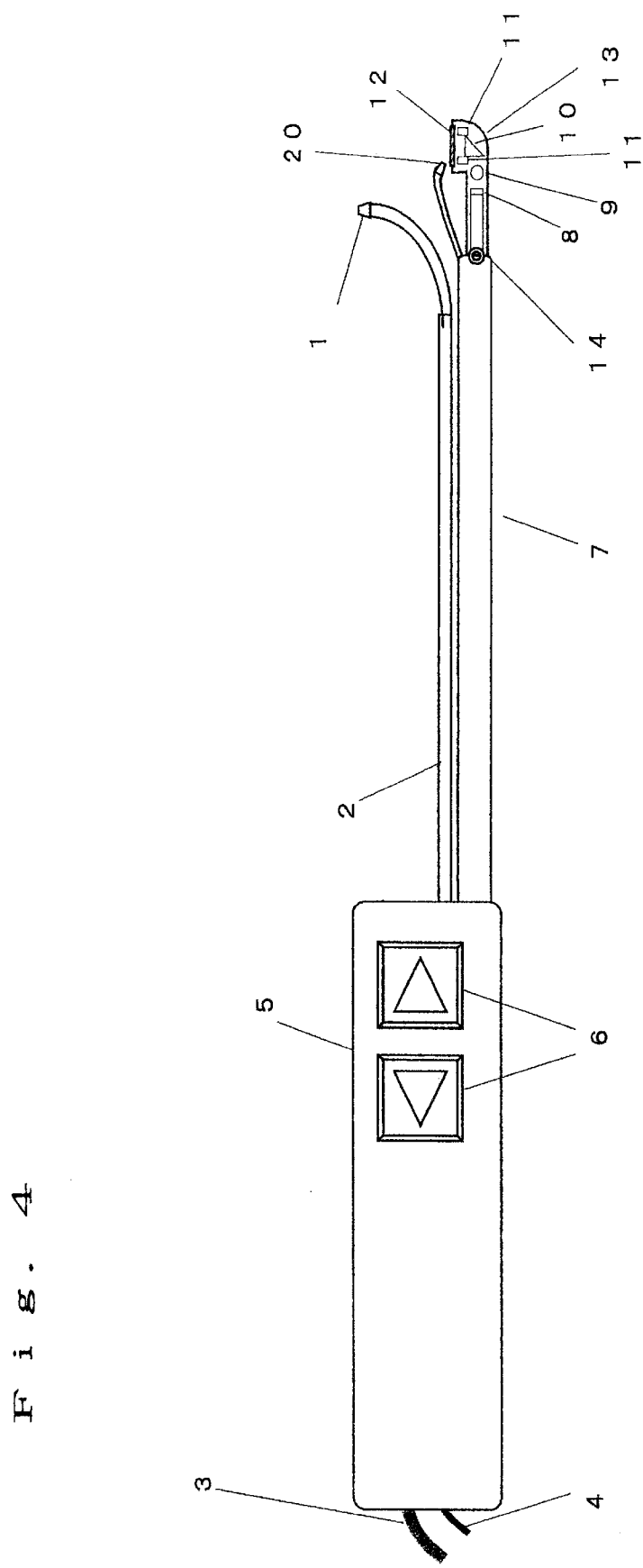
FIG. 4 is a side view showing a portion of an oral cavity washer with a video scope according to the second to fifth embodiments of the present invention.

FIG. 4 is a side view showing a portion of an oral cavity washer with a video scope according to a second embodiment of the present invention except for the display (display 17). In FIG. 4, reference numerals 1 to 14 denote the same objects as those denoted by reference numerals 1 to 14 of FIG. 1, and have the same functions. Reference numeral 20 denotes a nozzle, which jets liquid such as water to the optical window 12. This liquid is sent from the main body 16 to the grip portion 5 through the tube 3, and is sent from the grip portion 5 to the nozzle 20 through the pipe housed in the video scope base 7. Jetting of liquid for washing this optical window 12 is controlled by a switch 6 provided at the grip portion 5 as described below.

During the washing operation for the object using liquid from the nozzle 1, bubbles or water droplets are prone to occur, and these bubbles or water droplets may adhere to the optical window 12 to hinder the image pick-up. At this time, the switch 6 is operated to jet the liquid to the optical window 12 from the nozzle 20 for removing the adhered bubbles or water droplets. At a point of time whereat this removal can be confirmed by an image picked up, the control switch 6 can be operated to stop the jetting of the liquid from the nozzle 20.

As described above, the optical window 12 is provided with the nozzle 20, which is means of jetting the liquid, and this nozzle 20 is controlled, whereby when bubbles or water droplets adhere to the optical window 12 to hinder the image pick-up during the washing operation while actually confirming on the image that a place which has been observed with the video scope coincides with a place, to which the liquid is jetted, those bubbles or water droplets can be removed. Thereby, it is possible to confirm with a stable image even during the washing operation, and the practical effect is very great.

In this respect, it may also be gas, not liquid, that is jetted from the nozzle 20. In short, it will suffice if only it is fluid.

(Third Embodiment)

With reference to FIG. 4, the description will be made of a third embodiment according to the present invention.

In the second embodiment, when bubbles or water droplets adhere to the optical window 12 to hinder the image pick-up during the washing operation, the switch 6 has been operated to jet the liquid to the optical window 12 from the nozzle 20 for removing the adhered bubbles or water droplets. At this time, when the jetting velocity of the liquid from the nozzle 1 to the washing object is high among others, bubbles or water droplets may adhere to the optical window 12 in a moment by rebounding even after removal due to jetting of the liquid from the nozzle 20 to hinder the image pick-up.

In order to cope with such a case, according to the present embodiment, the nozzle 1 and the nozzle 20 automatically jet the liquid alternately. The liquid sent by a pump installed in the main body 16 is controlled by a change-over valve installed within the grip portion 5, whereby the liquid can be alternately jetted from the nozzle 1 and the nozzle 20. In the case where one pump is installed within the main body 16 as described above, it is possible to remove any bubbles or water droplets on the optical window 12 without reducing an amount of jet from the nozzle 1 and the velocity by alternately jetting.

As described above, the nozzle 20, which is the meams of jetting the liquid to the optical window 12, and the nozzle 1, which jets the liquid to the washing object, alternately jet the liquid, whereby the amount of jet from the nozzle 1 and the velocity are not reduced even in the case of one pump, but the practical effect is very great.

(Fourth Embodiment)

With reference to FIG. 4, the description will be made of a fourth embodiment according to the present invention.

In the present embodiment, on jetting the liquid from the nozzle 1 for washing, the liquid is caused to pulsate. In other words, the amount of jetting and/or the velocity of the liquid from the nozzle 1 are caused to change, for example, periodically. As described above, the instantaneous maximum amount of jetting and velocity are caused to increase for improving the washing effect and exhibiting a massage effect. Such a pulsation is synchronized with switching timing when the nozzle 1 and the nozzle 20 automatically jet the liquid alternately. Thereby, as in the third embodiment, even in the case of one pump, bubbles or water droplets on the optical window 12 can be removed without reducing the jet velocity of the nozzle 1. Further, the present embodiment is advantageous in the practical use because it is prone to be used together with the conventional pulsating operation.

Also, when the pulsating frequency is set at about 20 Hz or higher, a visual perception degree for the alternate jetting to this washing object and the optical window 12 is decreased, and therefore, continuous observation can be performed without any discomfort.

As described above, jetting to the washing object is caused to pulsate, and this jetting is caused to synchronize with the switching timing between the nozzle 1 and the nozzle 20, whereby bubbles and water droplets on the optical window 12 can be removed without reducing the amount of jetting from the nozzle 1 and the velocity even in the case of one pump. Further, the configuration of the mechanism is advantageous in the practical use. Also, continuous observation can be performed without any discomfort, and the practical effect is quite great.

(Fifth Embodiment)

With reference to FIG. 4, the description will be made of a fifth embodiment according to the present invention.

In the present embodiment, the nozzle 1 and the nozzle 20 automatically jet the liquid alternately as shown in the third and fourth embodiments, but it is characterized in that the amount of jetting from the nozzle 20 for jetting to the optical window 12 and the velocity are caused to be reduced lower than the nozzle 1.

A flow rate and flow velocity required to remove bubbles or water droplets may be sufficiently lower than a flow rate and flow velocity required to wash. Therefore, particularly in the case of one pump, the amount of jetting from the nozzle 20 and velocity are reduced, whereby the amount of jetting from the nozzle 1 and the velocity can be increased as a result. In other words, the amount of jetting from the nozzle 20 and the velocity are limited, whereby the jetting capacity can be accumulated during a period of time for jetting from the nozzle 20.

As described above, the nozzle 20, which is meams of jetting the liquid, and the nozzle 1, which jets the liquid to the washing object, alternately jet the liquid to the optical window 12 to reduce the amount of jetting from the nozzle 20 and the velocity, whereby even in the case of one pump, the amount of jetting from the nozzle 1 and the velocity can be sufficiently secured, and the practical effect is very great.

In this respect, in the above described second to fifth embodiments, the nozzle 20 for removing deposit onto the optical window 12 has been separately provided from the nozzle 1, but it may be possible to cause the nozzle 1 to have the function of the nozzle 20, and not to provide the nozzle 20.

(Sixth Embodiment)

Figure 5:
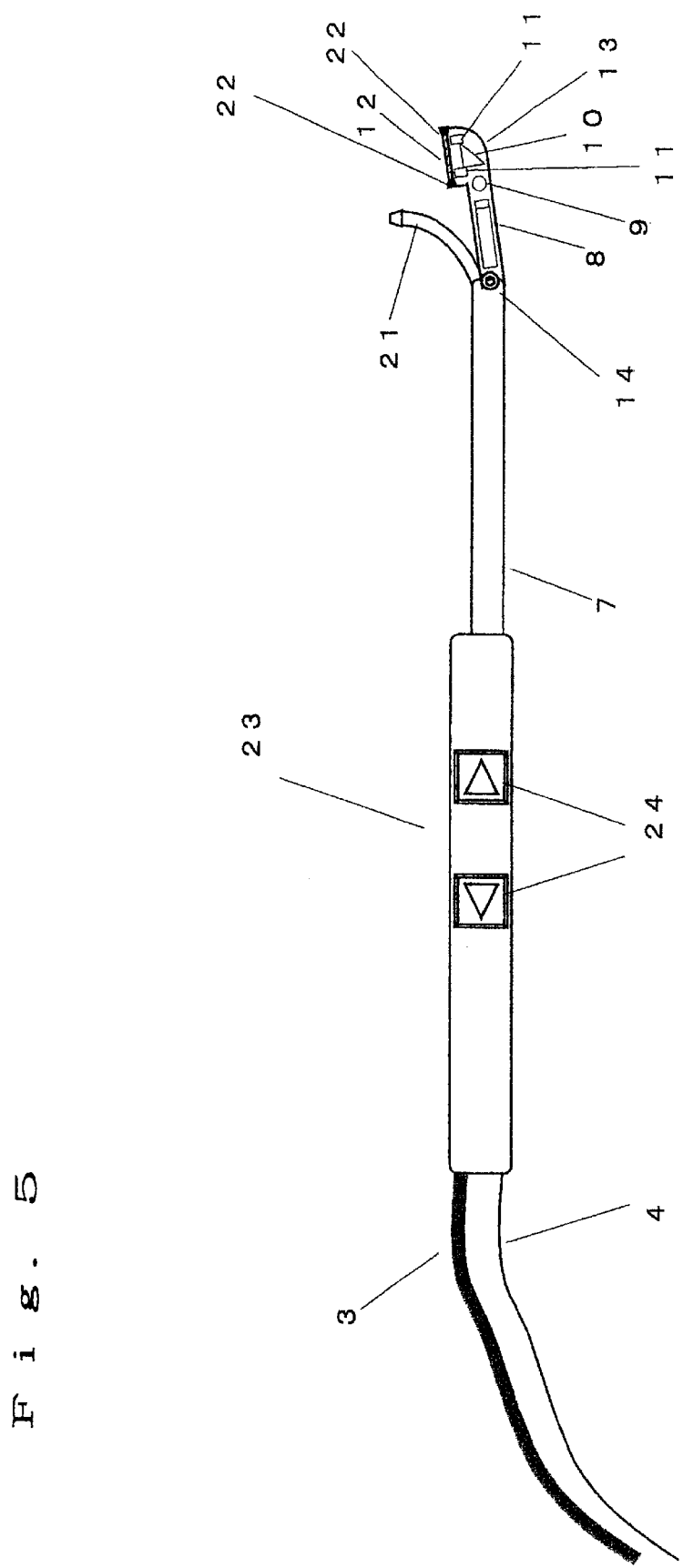
FIG. 5 is a side view showing a portion of an oral cavity washer with a video scope according to a sixth embodiment of the present invention.

FIG. 5 is a side view showing a portion of an oral cavity washer with a video scope according to a sixth embodiment of the present invention except for a display (display 17). Reference numerals 3,4 and 7 to 14 of FIG. 5 denote the same components as those denoted by reference numerals 3,4 and 7 to 14 of FIG. 1 disposed similarly.

Reference numeral 21 denotes a nozzle for jetting the liquid to the object, which jets the liquid supplied from the main body through a pipe installed within a video scope base 7, a grip portion 23 and a tube 3. Reference numeral 23 denotes a grip portion, and reference numeral 24 denotes a control switch provided in the grip portion 23, for controlling jetting and the like. The grip portion 23 shown in the present embodiment cannot be provided with a toothbrush, but can be made that much smaller than the grip portion 5, and has improved ease of operation. In FIG. 5, reference numeral 22 denotes a piezo-electric vibrator made of, for example, barium titanate porcelain, which micro-vibrates the optical window 12 at a frequency of, for example, 28 KHz. The operation of this piezo-electric vibrator 22 is controlled by the control switch 24.

When bubbles or water droplets, which have occurred during a washing operation, adhere to the optical window 12 to hinder the image pick-up, the switch 24 is operated to micro-vibrate the piezo-electric vibrator 22 to remove the bubbles or water droplets adhered to the optical window 12. At a point of time whereat the removal can be confirmed by the pick-up image or the like, the control switch 24 is operated to stop the micro-vibration.

Also, when micro-vibration is caused to be performed so as to make it difficult for bubbles or water droplets to adhere with commencement of the washing operation, the effect is further improved.

When there is provided means of micro-vibrating the optical window 12 and this means is controlled as described above, whereby bubbles or water droplets adhere to the optical window 12 to hinder the image pick-up during the washing operation while actually confirming on an image that a place which has been observed with the video scope coincides with a place, to which the liquid is jetted, these can be removed. Thereby, it is possible to confirm on a stable image even during the washing operation, and the practical effect is very great.

In this respect, in the above described sixth embodiment, the piezo-electric vibrator 22 has been made of barium titanate porcelain, but the material for the piezo-electric vibrator 22 is not limited to the barium titanate porcelain. In short, the piezo-electric vibrator 22 may be made of any material so long as it vibrates the optical window 12. Also, the piezo-electric vibrator 22 has vibrated the optical window 12 at a frequency of, for example, 28 KHz, but the vibration frequency is not limited to 28 KHz.

(Seventh Embodiment)

The present embodiment is configured as shown in FIG. 5 as in the sixth embodiment, but the optical window 12 has been subjected to the water-repellent treatment. Concretely, the outside surface of the optical window 12 is made water-repellent using a silane coupling agent having straight alkyl chain represented by $CF_3(CF_2)_n(CH_2)_2SiCl_3$ (where n is 0 or an integer of 1 or higher) or the like. The film thickness of this water-repellent treatment is 10 nm or less, and actually transmits visible light completely.

When bubbles or water droplets, which have occurred during a washing operation, adhere to the optical window 12 to hinder the image pick-up, the switch 24 is operated to micro-vibrate the piezo-electric vibrator 22 to remove the bubbles or water droplets adhered to the optical window 12. At a point of time whereat the removal can be confirmed by the pick-up image or the like, the control switch 24 is operated to stop the micro-vibration. At this time, since the optical window 12 has been subjected to the water-repellent treatment, it is easy to remove the bubbles or water droplets.

As described above, it is easy to remove the bubbles or water droplets by making the optical window 12 water-repellent, and even during the washing operation, it is possible to confirm with a stable image, and the practical effect is very great.

Also, as the water-repellent treatment, there has been shown an example using the silane coupling agent having straight alkyl chain represented by $CF_3(CF_2)_n(CH_2)_2SiCl_3$ (where n is 0 or an integer of 1 or higher) or the like, but even dimethyl silicone-based organic polymer water repellant is capable of obtaining an effect that it is made easier to remove deposit such as bubbles if only transmission of visible light is secured.

In this respect, in the present embodiment, there has been shown an example in which the optical window 12 subjected to the water-repellent treatment is micro-vibrated to thereby remove bubbles or water droplets, but this water-repellent treatment is similarly effective even when gas or liquid is jetted to the optical window 12 to thereby remove bubbles or water droplets.

(Eighth Embodiment)

In the present embodiment, the optical window 12 in FIGS. 1, 2, 4 and 5 has been subjected to a hydrophilic treatment.

Since the outside surface of the optical window 12 has been subjected to the hydrophilic treatment, bubbles or water droplets are prone to be collapsed, and it is difficult to hinder the image pick-up. In addition, this hydrophilic treatment has a defogging effect, it is possible to prevent the pick-up image from being clouded at the commencement of use, and the practical effect is very great.

As described above, in an oral cavity washer with a video scope according to each embodiment of the present invention, it is possible to perform maintenance operations such as observation and check on the interior of the oral cavity, and tooth cleaning at the same time, and the practical effect is very great.

In this respect, in each of the above described embodiments, the description has been made of a case where the nozzle 1 or the nozzle 21 jets liquid, but it may jet a gas. In short, the nozzle 1 or the nozzle 21 has only to wash the object such as the teeth or gums by jetting fluid.

The display 17 may be mounted by embedding it in a portion of a mirror in a toilet room among others, or may be mounted onto the user's head.

As seen from the above description, according to the present invention, it is possible to provide an oral cavity washer with a video scope capable of washing the interior of the oral cavity while actually confirming on the image that a place which the operator has observed with the video scope coincides with a place, to which the fluid is jetted.

What is claimed is:

1. An oral cavity washer with a video scope, comprising:
   a video scope having image-forming apparatus forming an image from light from an object, and an image pick-up device for converting the light from which the image is formed into an electric signal;
   a grip portion;
   an oral cavity washer for jetting a fluid to wash an oral cavity; and
   a display of displaying an image picked up by said video scope, said display displaying an aiming marker for indicating a target point of said fluid on an image picked up by said video scope.

2. The oral cavity washer with a video scope according to claim 1, further comprising an illuminating device for illuminating said object.

3. The oral cavity washer with a video scope according to claim 1, wherein said video scope has an optical window for transmitting light from said object and a removal device for removing any deposit on said optical window, and said image-forming apparatus forms an image from light from said object which transmits through said optical window.

4. The oral cavity washer with a video scope according to claim 3, wherein said removal device provides jetting the fluid onto said optical window.

5. The oral cavity washer with a video scope according to claim 4, wherein said oral cavity washer causes said fluid to pulsate, and said fluid is alternately jetted onto said object and said optical window in synchronism with the pulsation.

6. The oral cavity washer with a video scope according to claim 4, wherein said oral cavity washer serves as said jetting device.

7. The oral cavity washer with a video scope according to claim 3, further comprising control means provided in said grip portion for controlling operation of said removal device.

8. The oral cavity washer with a video scope according to claim 3, wherein said optical window is subjected to a water-repellent treatment, which permits transmission of visible light.

9. The oral cavity washer with a video scope according to claim 8, wherein said water-repellent treatment includes a compound selected from the group consisting of dimethyl silicone-based organic polymer water repellent and silane coupling agent having straight alkyl chain.

10. The oral cavity washer with a video scope according to claim 3, wherein said optical window is subjected to a hydrophilic treatment, which permits transmission of visible light.

11. The oral cavity washer with a video scope according to claims 1–10, wherein said display is provided on a charger for charging an apparatus installed in said grip portion, or on an installation apparatus on which said grip portion is installed when the oral cavity washer is not used.

12. An oral cavity washer with a video scope comprising:
    a video scope having image-forming apparatus forming an image from light from an object, and an image pick-up device for converting the light from which the image is formed into an electric signal;
    a grip portion;
    a display of displaying an image picked up by said video scope; and
    a toothbrush portion having a brush portion.

13. An oral cavity washer with a video scope comprising:
    a video scope having an optical window for transmitting light from an object, image-forming apparatus forming an image from said light, and an image pick-up device for converting said light into an electric signal;
    a grip portion;
    a display of displaying an image picked up by said video scope; and
    an oral cavity washer for alternately jetting a fluid onto said object and said optical window for removing a deposit on said optical window.

14. An oral cavity washer with a video scope comprising:
    a video scope having an optical window for transmitting light from an object, image-forming apparatus forming an image from said light, an image pick-up device for converting said light into an electric signal, and a jetting device of jetting a fluid to remove a d eposit on said optical window;
    a grip portion;
    a display of displaying an image picked up by said video scope; and
    an oral cavity washer for jetting said fluid to wash an oral cavity, said oral cavity washer having a higher jetting velocity of said fluid than said jetting device.

15. An oral cavity washer with a video scope comprising:
    a video scope having an optical window for transmitting light from an object, image-forming apparatus forming an image from said light, an image pick-up device for converting said light into an electric signal, and a device of vibrating said optical window to remove a deposit on said optical window;
    a grip portion;
    a display of displaying an image picked up by said video scope; and
    an oral cavity washer for jetting a fluid to wash an oral cavity.

* * * * *

UNITED STATES PATENT AND TRADEMARK OFFICE
CERTIFICATE OF CORRECTION

PATENT NO. : 6,468,076 B2 Page 1 of 1
DATED : October 22, 2002
INVENTOR(S) : Taturou Kawamura It is certified that error appears in the above-identified patent and that said Letters Patent is hereby corrected as shown below:

Title page,
Item [57], ABSTRACT, should read as follows:
-- An oral cavity washer with a video scope, has a video scope having image-forming apparatus forming an image from light from an object. An image pick-up device converts the light from which the image is formed by the image-forming apparatus into an electric signal. A first grip portion is held by an operator.

A display displays an image picked up by the video scope.

An oral cavity washer having a nozzle for jetting a fluid and a grip portion for being held by the operator, washes an oral cavity by jetting the fluid to teeth or gums. --

Item [75], Inventors, delete "Kyotanabe" and substitute therefor -- Kyoto --.

Column 9,
Line 58, "4" should read -- 13 --.

Signed and Sealed this

Twenty-seventh Day of May, 2003

JAMES E. ROGAN
*Director of the United States Patent and Trademark Office*